US009499789B2

(12) United States Patent
Nakahata et al.

(10) Patent No.: US 9,499,789 B2
(45) Date of Patent: Nov. 22, 2016

(54) METHOD FOR PRODUCING DENDRITIC CELLS FROM PLURIPOTENT STEM CELLS

(75) Inventors: Tatsutoshi Nakahata, Kyoto (JP); Megumu Saito, Kyoto (JP); Akira Niwa, Kyoto (JP); Masakatsu Yanagimachi, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/001,004

(22) PCT Filed: Feb. 23, 2012

(86) PCT No.: PCT/JP2012/055152
§ 371 (c)(1),
(2), (4) Date: Aug. 22, 2013

(87) PCT Pub. No.: WO2012/115276
PCT Pub. Date: Aug. 30, 2012

(65) Prior Publication Data
US 2013/0330822 A1    Dec. 12, 2013

Related U.S. Application Data

(60) Provisional application No. 61/445,856, filed on Feb. 23, 2011.

(51) Int. Cl.
*C12N 5/0784*    (2010.01)
(52) U.S. Cl.
CPC ......... *C12N 5/0639* (2013.01); *C12N 2500/25* (2013.01); *C12N 2500/90* (2013.01); *C12N 2501/145* (2013.01); *C12N 2501/155* (2013.01); *C12N 2501/22* (2013.01); *C12N 2501/26* (2013.01); *C12N 2506/02* (2013.01); *C12N 2506/45* (2013.01)

(58) Field of Classification Search
CPC .............. C12N 5/0639; C12N 5/0662; A61K 39/0011
See application file for complete search history.

(56) References Cited

U.S. PATENT DOCUMENTS

| 5,843,780 | A | 12/1998 | Thomson | |
|---|---|---|---|---|
| 5,994,126 | A * | 11/1999 | Steinman et al. | 435/325 |
| 6,479,286 | B1 * | 11/2002 | Nelson et al. | 435/377 |
| 8,048,999 | B2 | 11/2011 | Yamanaka et al. | |

FOREIGN PATENT DOCUMENTS

| WO | WO 95/34638 A1 | 12/1995 |
|---|---|---|
| WO | WO 2006/020889 A2 | 2/2006 |
| WO | WO 2006/022330 A1 | 3/2006 |
| WO | WO 2007/069666 A1 | 6/2007 |
| WO | WO 2008/048671 A1 | 4/2008 |
| WO | WO 2009/120891 A2 | 10/2009 |
| WO | WO 2010/096746 A1 | 8/2010 |
| WO | WO 2010/099539 A1 | 9/2010 |

OTHER PUBLICATIONS

International Search Report and Written Opinion of the International Searching Authority for International Application No. PCT/JP2012/055152, mailed on May 22, 2012.
Senju et al., "Genetically Manipulated Human Embryonic Stem Cell-Derived Dendritic Cells with Immune Regulatory Function," *Stem Cells*, vol. 25, pp. 2720-2729 (2007).
Senju et al., "Pluripotent stem cells as source of dendritic cells for immune therapy," *Int. J. Hematol*, vol. 91(3), pp. 392-400 (2010).
Zhan et al., "Functional antigen-presenting leucocytes derived from human embryonic stem cells in vitro," *The Lancet*, vol. 364, pp. 163-171 (Jul. 10, 2004).
Extended European Search Report for European Patent Application No. 12749212.2, issued on Dec. 22, 2014.
Umeda et al., "Development of primitive and definitive hematopoiesis from non-human primate embryonic stem cells in vitro," *Development*, vol. 131(8), pp. 1869-1879 (2004).
Yanagimachi et al., "Robust and Highly-Efficient Differentiation of Functional Monocytic Cells from Human Pluripotent Stem Cells under Serum- and Feeder Cell-Free Conditions," *PLOS ONE*, vol. 8(4), p. e59243 (Apr. 2013).

* cited by examiner

*Primary Examiner* — Laura Schuberg
(74) *Attorney, Agent, or Firm* — Knobbe, Martens, Olson & Bear, LLP

(57) ABSTRACT

A dendritic cell is produced from pluripotent stem cells by culturing pluripotent stem cells by the following steps: (1) performing adherent culture in a medium which comprises a BMP family protein but does not comprise serum; (2) performing adherent culture in a medium which comprises VEGF but does not comprise serum; (3) performing adherent culture in a medium which comprises a hematopoietic factor but does not comprise serum; and (4) performing suspension culture in a medium which does not comprise serum.

18 Claims, 3 Drawing Sheets

METHOD FOR PRODUCING DENDRITIC CELLS FROM PLURIPOTENT STEM CELLS

CROSS-REFERENCE TO RELATED APPLICATIONS

This application is the U.S. National Phase under 35 U.S.C. §371 of International Application PCT/JP2012/055152, filed Feb. 23, 2012, which claims priority to U.S. Provisional Application No. 61/445,856, filed Feb. 23, 2011.

TECHNICAL FIELD

The present invention relates to a method for efficiently producing dendritic cells from pluripotent stem cells, and dendric cells produced thereby.

BACKGROUND ART

The dendric cell is one of the strongest cells among the antigen-presenting cells that play important roles in priming of naive T cells, and the like. In view of this, application of dendritic cells pulsed with an antigen to cancer immunotherapy has been proposed (WO1995/034638).

On the other hand, cells having pluripotency, such as embryonic stem cells (ES cells), and induced pluripotent stem cells (iPS cells) obtained by introducing undifferentiated cell-specific genes into somatic cells have been reported so far (U.S. Pat. No. 5,843,780 B or WO 2007/069666). Therefore, recent interest has focused on regenerative medicine wherein dendritic cells obtained by differentiation induction of these pluripotent stem cells are transplanted, and preparation of a pathologic model in vitro using these dendritic cells.

As a method for preparing dendritic cells from ES cells or iPS cells, a method wherein an embryoid body is formed in a medium supplemented with a cytokine so as to induce dendritic cells (Zhan X, et al, Lancet. 2004, 364, 163-71), or a method wherein those cells are cultured on stromal cells derived from a different species (Senju S, et al, Stem Cells. 2007, 25, 2720-9) has been used. However, in the method wherein the induction is achieved via an embryoid body, only a part of the cells become the cells of interest, while most of the others are induced to differentiate into other cell types, resulting in a low induction efficiency. Further, in cases where cells derived from a different species are used, it is difficult to use the induced cells for transplantation. Further, in cases where a pathologic model is prepared, it is preferred to avoid use of culture conditions accompanied by uncertainties such as lot-to-lot variation, as much as possible.

However, it has not been reported so far that dendritic cells are prepared from pluripotent stem cells by a method using a medium containing only limited components without forming an embryoid body or coculturing with cells from a different species.

SUMMARY OF THE INVENTION

The present invention aims to efficiently produce dendritic cells from pluripotent stem cells using limited components. Therefore, an object of the present invention is to provide culture conditions that allow induction of differentiation of human pluripotent stem cells, especially human induced pluripotent stem cells into dendritic cells.

In order to solve the above-described problems, the present inventors discovered that the dendritic cells of interest can be obtained by performing adherent culture and suspension culture of pluripotent stem cells, under conditions without feeder cells, that is, in a medium which contains BMP4, VEGF and various hematopoietic factors but does not contain serum, while appropriately exchanging the medium.

From the above results, the present inventors cultured pluripotent stem cells under appropriate culture conditions and succeeded in production of dendritic cells under limited conditions, thereby completing the present invention.

That is, the present invention is as follows.

It is an aspect of the present invention to provide a method for producing dendritic cells from pluripotent stem cells, said method comprising culturing pluripotent stem cells by the steps below:

(1) performing adherent culture using a medium which comprises the BMP family protein but does not comprise serum;

(2) performing adherent culture using a medium which comprises VEGF but does not comprise serum;

(3) performing adherent culture using a medium which comprises a hematopoietic factor but does not comprise serum; and (4) performing suspension culture using a medium which does not comprise serum.

It is another aspect of the present invention to provide the method as described above, wherein said adherent culture in said Steps (1) to (3) is performed in an extracellular matrix-coated dish.

It is another aspect of the present invention to provide the method as described above, wherein said extracellular matrix is Matrigel.

It is another aspect of the present invention to provide the method as described above, wherein said BMP family protein is BMP4.

It is another aspect of the present invention to provide the method as described above, wherein in said Step (2), said culturing is performed in a medium further comprising bFGF and/or SCF.

It is another aspect of the present invention to provide the method as described above, wherein said hematopoietic factor is at least one selected from the group consisting of SCF, TPO, IL-3, Flt3-ligand, GM-CSF and M-CSF.

It is another aspect of the present invention to provide the method as described above, wherein, in said Step (3), said culturing is performed in a medium comprising SCF, TPO, IL-3 and Flt3-ligand, and then in a medium comprising GM-CSF, M-CSF and Flt3-ligand.

It is another aspect of the present invention to provide the method as described above, wherein, in said Step (3), said culturing is performed in a medium comprising SCF, TPO, IL-3 and Flt3-ligand, and then in a medium comprising SCF, Flt3-ligand, GM-CSF and M-CSF.

It is another aspect of the present invention to provide the method as described above, wherein, in said Step (4), said suspension culture is performed in a medium comprising GM-CSF and IL-4.

It is another aspect of the present invention to provide the method as described above, wherein, in said Step (4), suspension culture in a medium comprising LPS and TNF-α is further performed.

It is another aspect of the present invention to provide the method as described above, wherein said dendritic cell is positive for HLA-DR and negative for CD14.

It is another aspect of the present invention to provide the method as described above, wherein said dendritic cell is positive for CD83.

It is another aspect of the present invention to provide the method as described above, wherein said Step (1) is performed for 4 days.

It is another aspect of the present invention to provide the method as described above, wherein said Step (2) is performed for 2 days.

It is another aspect of the present invention to provide the method as described above, wherein said pluripotent stem cell is a human iPS cell.

It is another aspect of the present invention to provide dendritic cells produced by the method as described above.

DESCRIPTION OF THE EMBODIMENT OF THE INVENTION

Figure 1:
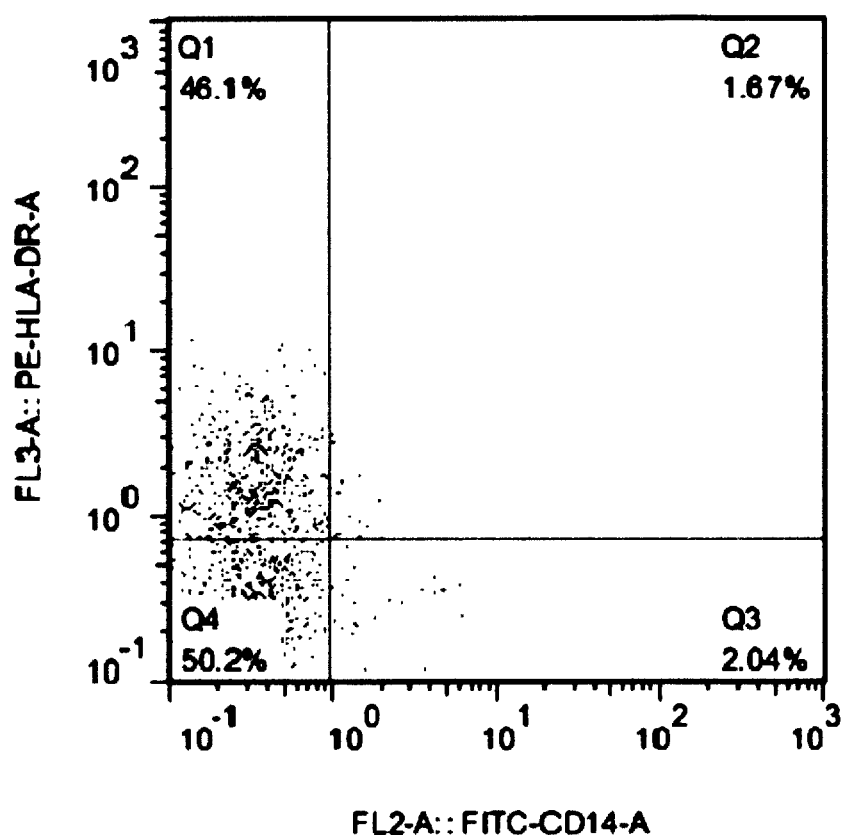
FIG. 1 shows results of flow cytometry of cells obtained after 6 days of suspension culture of CD14-positive cells.

The present invention will now be described below in detail.

The present invention relates to, as described above, a method for producing cells including dendritic cells from pluripotent stem cells, which method comprises: (1) performing adherent culture in a medium which comprises the BMP family protein but does not comprise serum; (2) performing adherent culture in a medium which comprises VEGF but does not comprise serum; (3) performing adherent culture in a medium which comprises a hematopoietic factor but does not comprise serum; and (4) performing suspension culture in a medium which does not comprise serum; and thereby dendritic cells are obtained.

<Pluripotent Stem Cells>

The pluripotent stem cells which may be used in the present invention are stem cells having pluripotency which enables the cells to differentiate into any cells existing in the living body, as well as growth ability. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells") and induced pluripotent stem (iPS) cells. Preferred examples of the pluripotent stem cells include ES cells, ntES cells and iPS cells.

(A) Embryonic Stem Cells

ES cells are stem cells established from the inner cell mass of an early embryo (for example, blastocyst) of a mammal such as human or mouse, and ES cells have pluripotency and growth ability by self-renewal.

ES cells are embryo-derived stem cells originated from the inner cell mass of a blastocyst which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of the subject animal, followed by culturing the inner cell mass on fibroblasts as feeders. The cells can be maintained by subculturing using a medium supplemented with substances such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml β-FGF, at 37° C. in 2% $CO_2$/98% air under a moist atmosphere (O. Fumitaka et al. (2008), Nat. Biotechnol., 26:215-224). Further, ES cells need to be subcultured every 3 to 4 days, and the passage of cells can be performed using 0.25% trypsin and 0.1 mg/ml collagenase IV in PBS supplemented with 1 mM $CaCl_2$ and 20% KSR.

Selection of ES cells can be generally performed by the Real-Time PCR method using as an index/indices expression of a gene marker(s) such as alkaline phosphatase, Oct-3/4 and/or Nanog. In particular, for selection of human ES cells, expression of a gene marker(s) such as OCT-3/4, NANOG and/or ECAD can be used as indices (E. Kroon et al. (2008), Nat. Biotechnol., 26:443-452).

For example, in terms of human ES cell lines, WA01(H1) and WA09(H9) can be obtained from WiCell Research Institute, and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similar to ES cells.

They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors are in the forms of DNAs or proteins. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of the genes of the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2 and Tbx3, and these reprogramming factors may be used either alone or in combination. Examples of the combinations of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010); and Stem Cells. 28:713-720.

Examples of reprogramming factors also include histone deacetylase (HDAC) inhibitors [for example, low molecular weight inhibitors such as valproic acid (VPA), trichostatin A, sodium butyrate, MC 1293 and M344; and nucleic acid-type expression inhibitors such as siRNAs and shRNAs against HDAC (e.g., HDAC1 siRNA Smartpool® (Millipore) and HuSH 29mer shRNA Constructs against HDAC1 (Ori-Gene))], MEK inhibitors (for example, PD184352, PD98059, U0126, SL327 and PD0325901), Glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1 and G9a), L-channel calcium agonists (for example, Bayk8644), butyric acid, TGFβ inhibitors or ALK5 inhibitors (for example, LY364947, SB431542, 616453 and A-83-01), p53 inhibitors (for example, siRNAs and shRNAs against p53), ARID3A inhibitors (for example, siRNAs and shRNAs against ARID3A), miRNAs such as miR-291-3p, miR-294, miR-295 and mir-302, Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2 and DMRTB1, which are employed for enhancing the establishment efficiency, and, in the present description, these factors employed for the purpose of enhancement of the establishment efficiency are not particularly distinguished from the above-described reprogramming factors.

In cases where the reprogramming factors are in the form of protein, each reprogramming factor may be introduced into somatic cells by a method such as lipofection, fusion with a cell-permeable peptide (e.g., HIV-derived TAT or polyarginine), or microinjection.

In cases where the reprogramming factors are in the form of DNA, each reprogramming factor may be introduced into somatic cells by a method such as use of a vector including virus, plasmid and artificial chromosome vectors; lipofection; use of liposome; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site to enable expression of the nuclear reprogramming factors; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; and/or the like. Further, in order to remove, after introduction of the above vector into somatic cells, the genes encoding the reprogramming factors, or both the promoters and the genes encoding the reprogramming factors linked thereto, the vector may have LoxP sequences in the upstream and the downstream of these sequences.

Further, in cases where the reprogramming factors are in the form of RNA, each reprogramming factor may be introduced into somatic cells by a method such as lipofection or microinjection, and an RNA into which 5-methylcytidine and pseudouridine (TriLink Biotechnologies) have been incorporated may be used in order to suppress degradation (Warren L, (2010) Cell Stem Cell. 7:618-630).

Examples of the medium for induction of the iPS cells include the DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the culture method include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in the DMEM medium supplemented with 10% FBS (this medium may further contain LIF, penicillin/streptomycin, puromycin, L-glutamine, non-essential amino acids, β-mercaptoethanol and/or the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349) or Matrigel (BD)) is used instead.

Other examples include a method wherein the culture is performed using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of not less than 0.1% and not more than 15%) (Yoshida Y, et al. (2009), Cell Stem Cell. 5:237-241 or WO2010/013845).

During the culture, the medium is replaced with a fresh medium once every day from Day 2 of the culture. The number of the somatic cells used for nuclear reprogramming is not restricted, and usually within the range of about $5 \times 10^3$ to about $5 \times 10^6$ cells per 100-$cm^2$ area on the culture dish.

iPS cells may be selected based on the shape of each formed colony. In cases where a drug resistance gene, which is expressed in conjunction with a gene being expressed upon reprogramming of a somatic cell (e.g., Oct3/4 or Nanog), is introduced as a marker gene, established iPS cells can be selected by culturing the cells in a medium containing the corresponding drug (selection medium). Further, iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of mammals including human) excluding germ-line cells and totipotent cells such as eggs, oocytes and ES cells. Examples of the somatic cells include, but are not limited to, any of fetal somatic cells, neonatal somatic cells, and mature, healthy and diseased somatic cells, as well as any of primary cultured cells, subcultured cells and established cell lines. Particular examples of the somatic cells include (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes.

In cases where iPS cells are used as a material for cells to be transplanted, somatic cells whose HLA genotype is the same or substantially the same as that of the individual to which the cells are to be transplanted are preferably used in view of prevention of the rejection reaction. Here, "substantially the same" means that the HLA genotype is matching to an extent at which the immune reaction against the transplanted cells can be suppressed with an immunosuppressive agent. For example, the somatic cells have matched HLA types at 3 loci HLA-A, HLA-B and HLA-DR, or at 4 loci further including HLA-C.

(E) ES Cells Derived from Cloned Embryo Obtained by Nuclear Transfer ntES cells are ES cells derived from a cloned embryo prepared by the nuclear transfer technique, and have properties which are almost the same as those of ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition):47-52). In nuclear transfer, reprogramming can be achieved by injecting the nucleus of a somatic cell into a mammalian enucleated unfertilized egg and culturing the resultant for several hours.

<Method for Producing Dendritic Cells from Pluripotent Stem Cells>

In the present invention, the dendritic cell is a tree-shaped or branch-shaped cell having cell processes, and is an immunocyte having an antigen-presenting capacity to T cells. Examples of the dendritic cell include the bone marrow-derived dendritic cell, plasmacytoid dendritic cell, Langerhans cell, interdigitating cell, veiled cell and dermal dendritic cell. The dendritic cell is preferably a bone marrow-derived dendritic cell which expresses at least one marker selected from the group consisting of surface antigens CD11a, MHC-classII (for example, in the case of human, HLA-DR, HLA-DP and HLA-DQ), CD40, CD80 and CD86. More preferably, the dendritic cell is positive for HLA-DR and CD83 and negative for CD14.

The method of the present invention for producing dendritic cells from pluripotent stem cells comprises culturing pluripotent stem cells by the steps below:

(1) performing adherent culture in a medium which comprises the BMP family protein but does not comprise serum;

(2) performing adherent culture in a medium which comprises VEGF but does not comprise serum;

(3) performing adherent culture in a medium which comprises a hematopoietic factor but does not comprise serum; and (4) performing suspension culture in a medium which does not comprise serum.

The "serum" herein means human serum, monkey serum, fetal bovine serum, bovine serum, pig serum, equine serum, donkey serum, chicken serum, quail serum, sheep serum, goat serum, dog serum, cat serum, rabbit serum, rat serum, guinea pig serum, mouse serum and the like, and the medium which does not comprise serum is preferably a medium having predetermined components and may contain at least one of albumin or an albumin alternative; transferrin or a transferrin alternative; insulin or an insulin alternative; and selenious acid. The medium which does not comprise serum is more preferably a medium supplemented with Insulin-Transferrin-Selenium-X Supplement (ITS) (Invitrogen). In the present invention, preferred examples of the medium which does not contain serum include minimum essential medium (MEM), Dulbecco's modified Eagle's medium (DMEM), Iscove's modification of Dulbecco's medium (IMDM), StemPro-34SFM (Invitrogen), Stemline II (Sigma-Aldrich) and the like which are supplemented with ITS; medium for culturing primate ES cells (medium for primate ES/iPS cells, ReproCELL) wherein a serum alternative has been preliminarily added; and serum-free medium (mTeSR, Stemcell Technology). The medium which does not comprise serum is more preferably Stemline II supplemented with ITS.

The "BMP family protein" is a group of proteins belonging to the TGF-β superfamily and includes about 20 subtypes of cytokines involved in osteogenesis, cell growth, cell differentiation, organ development, organogenesis and the like. In the present invention, the BMP family protein is preferably BMP2 and/or BMP4, more preferably BMP4.

The "VEGF" is a group of glycoproteins involved in vasculogenesis and angiogenesis, and examples thereof include VEGF-A, VEGF-B, VEGF-C, VEGF-D, VEGF-E, PlGF (placental growth factor)-1 and PlGF-2, and alternative splicing variants thereof (for example, variants of VEGF-A having 121, 165, 189 and 206 amino acids). In the present invention, the VEGF is preferably VEGF-A.

In the preferable embodiment of the above Step (2), the medium may further comprise the bFGF and/or SCF.

"Hematopoietic factor" is a factor that promotes differentiation and growth of blood cells, and examples thereof include the stem cell factor (SCF), granulocyte-colony stimulating factor (G-CSF), granulocyte-monocyte colony-stimulating factor (GM-CSF), macrophage colony-stimulating factor (M-CSF), erythropoietin (EPO), thrombopoietin (TPO), interleukins and Flt3 ligand. Here, interleukins are proteins secreted from leukocytes, and can be divided into not less than 30 types such as IL-1, IL-2, IL-3, IL-4, IL-5, IL-6, IL-7, IL-8 and IL-9. In the present invention, the hematopoietic factor is preferably selected from the group consisting of SCF, TPO, IL-3, Flt3-ligand, GM-CSF and M-CSF. In the present invention, the hematopoietic factor may be used alone (for example, GM-CSF alone), but a combination of hematopoietic factors is preferably used. In cases where hematopoietic factors are used in combination, for example, in the above Step (3), a combination of factors selected from the group consisting of SCF, TPO, IL-3 and Flt3-ligand is first employed, and then a combination of factors selected from the group consisting of SCF, GM-CSF, M-CSF and Flt3-ligand is employed as the hematopoietic factor. More preferably, the combination consisting of SCF, TPO, IL-3 and Flt3-ligand is first employed, and then the combination consisting of GM-CSF, M-CSF and Flt3-ligand is employed; or the combination consisting of SCF, TPO, IL-3 and Flt3-ligand is first employed, and then the combination consisting of SCF, GM-CSF, M-CSF and Flt3-ligand is employed.

Further, also in the above Step (4), a hematopoietic factor(s) may be contained, and examples of the hematopoietic factor(s) used in Step (4) include a combination of factors selected from the group consisting of GM-CSF and IL-4. Further, for maturation of the dendritic cells, lipopolysaccharide (LPS) and/or tumor necrosis factor may be used. Here, the lipopolysaccharide is a substance which is a component constituting the outer membrane of the cell wall of Gram-negative bacteria, and constituted by lipid and polysaccharide. The tumor necrosis factor is a cytokine selected from the group consisting of TNF-α, TNF-β (lymphotoxin(LT)-α) and LT-β, and is preferably TNF-α in the present invention.

Considering that the dendritic cells of interest can be obtained by performing Step (4) on myelomonocytic cells (CD14-positive cells) as an intermediate, and in view of enhancement of the efficiency of induction to dendritic cells, CD14-positive cells among the floating cells produced in the above step (3) are preferably purified to be employed in the above Step (4). The purification of CD14-positive cells can be performed by a method well known to those skilled in the art, and the method is not restricted. For example, the cells can be purified using CD14 MicroBeads (#130-050-201, Miltenyi Biotec) with autoMACS pro (Miltenyi Biotec) or flow cytometer. The floating cells to be used in Step (4) are preferably subjected to density gradient centrifugation using a flow cytometer, Lymphoprep (AXIS-SHIELD PoC AS) or the like to remove dead cells before use.

The concentration of the cytokine or the like, including the hematopoietic factor, to be used in each step is not restricted as long as the cells of interest can be obtained at the concentration, and, in the case of BMP4, the concentration may be 5 ng/ml to 150 ng/ml, and is preferably 10 ng/ml to 100 ng/ml, more preferably 20 ng/ml to 80 ng/ml. In the case of VEGF, the concentration may be 20 ng/ml to 100 ng/ml, and is preferably 30 ng/ml to 70 ng/ml, more preferably 50 ng/ml. In the case of bFGF, the concentration is 10 ng/ml to 100 ng/ml, preferably 20 ng/ml to 50 ng/ml, more preferably 25 ng/ml. In the case of SCF, the concentration is 20 ng/ml to 100 ng/ml, preferably 30 ng/ml to 70 ng/ml, more preferably 50 ng/ml. In the case of IL-3, the concentration is 5 ng/ml to 100 ng/ml, preferably 30 ng/ml to 70 ng/ml, more preferably 50 ng/ml. In the case of TPO, the concentration is 1 ng/ml to 25 ng/ml, preferably 1 ng/ml to 10 ng/ml, more preferably 5 ng/ml. In the case of Flt3-ligand, the concentration is 10 ng/ml to 100 ng/ml, preferably 30 ng/ml to 70 ng/ml, more preferably 50 ng/ml. In the case of GM-CSF, the concentration is 5 ng/ml to 100 ng/ml, preferably 10 ng/ml to 50 ng/ml, more preferably 25 ng/ml. In the case of M-CSF, the concentration is 5 ng/ml to 100 ng/ml, preferably 30 ng/ml to 70 ng/ml, more preferably 50 ng/ml. In the case of IL-4, the concentration is 5 ng/ml to 100 ng/ml, preferably 10 ng/ml to 70 ng/ml, more preferably 40 ng/ml. In the case of TNF-α, the concentration is 0.05 ng/ml to 1 ng/ml, preferably 0.1 ng/ml to 0.5 ng/ml, more preferably 0.2 ng/ml. In the case of LPS, the concentration is 0.01 μg/ml to 10 μg/ml, preferably 0.1 μg/ml to 1 μg/ml, more preferably 0.2 μg/ml.

In terms of the period of each step, the above Step (1) is performed for not less than 2 days, preferably for not less than 2 days and not more than 6 days, more preferably for 4 days. The above Step (2) is performed for not less than 1 day, preferably for not less than 1 day and not more than 5 days, more preferably for 2 days. The above Step (3) is performed for not less than 10 days, preferably for not less than 10 days and not more than 30 days, more preferably for 24 days. In cases where the combination of hematopoietic factors is changed in the above Step (3), the period when a combination of hematopoietic factors selected from the group consisting of SCF, TPO, IL-3 and Flt3-ligand is used is not less than 7 days, preferably not less than 7 days and not more than 14 days, more preferably 9 days; and the period when a combination of hematopoietic factors selected from the group consisting of SCF, GM-CSF, M-CSF and Flt3-ligand is used is not less than 3 days, preferably not less than 3 days and not more than 20 days, more preferably 15 days. In terms of the above Step (4), the period is not less than 3 days, preferably not less than 3 days and not more than 14 days, more preferably 7 days. In cases where a hematopoietic factor(s) is used in the above Step (4), the culture period when a hematopoietic factor(s) selected from the group consisting of GM-CSF and IL-4 is/are used is not less than 3 days, preferably not less than 3 days and not more than 10 days, more preferably 5 days; and in cases where a combination of factors selected from TNF-α and LPS is further added, the culture period is not less than 1 day, preferably not less than 1 day and not more than 7 days, more preferably 2 days.

EXAMPLES

The present invention will now be described more concretely by way of Examples below, but the scope of the present invention is not restricted to these examples.

Human ES cells (KhES-1) were received from Institute for Frontier Medical Sciences, Kyoto University, and human iPS cells (201B7 and 253G4) were received from Prof. Yamanaka at Kyoto University. The human ES cells and the human iPS cells were cultured on dishes coated with growth factor-reduced Matrigel (#354230; Becton-Dickinson) using mTeSR1 (#05850; STEMCELL Technologies).

Example 1

By the following method, human iPS cells (253G4) were induced to differentiate into dendritic cells through CD14-positive monocyte, and the obtained dendritic cells were then analyzed by flow cytometry. As a result, it was confirmed that CD14-negative HLA-DR-positive cells were contained (FIG. 1).
1. iPS cell colonies were plated on a 6-well plate coated with growth factor-reduced Matrigel such that not more than 5 colonies were contained in each well, and cultured using mTeSR1 until the diameter of each colony became about 1 mm.
2. The medium was replaced with Stemline II serum-free hematopoietic stem cell expansion medium (Stemline II) (#S0192; Sigma-Aldrich) supplemented with Insulin-Transferrin-Selenium-X Supplement (ITS) (#51500-056; Invitrogen) and 20 ng/mL BMP4 (#314-BP-010; R&D Systems), and the cells were cultured for 4 days.
3. The medium was replaced with Stemline II supplemented with ITS, 50 ng/mL VEGF (#293-VE-050; R&D Systems) and 50 ng/mL SCF (#255-SC-050; R&D Systems), and the cells were cultured for 2 days.
4. The medium was replaced with Stemline II supplemented with ITS, 50 ng/mL SCF, 50 ng/mL IL-3 (#203-IL-050; R&D Systems), 5 ng/mL TPO (#288-TPN-025; R&D Systems) and 50 ng/mL Flt-3 ligand (#308-FK-025; R&D Systems), and the cells were cultured for 7 to 9 days.
5. The medium was replaced with Stemline II supplemented with ITS, 50 ng/mL Flt-3 ligand, 25 ng/mL GM-CSF and 50 ng/mL M-CSF, and the cells were cultured for 15 days. During this culture, the medium was replaced with fresh medium every 5 days.
6. Floating cells in the culture supernatant were collected, and dead cells were removed by density gradient centrifugation using Lymphoprep (#1114740; AXIS-SHIELD PoC AS), followed by separation of CD14-positive cells using CD14 MicroBeads (#130-050-201, Miltenyi Biotec) with autoMACS pro (Miltenyi Biotec). The separated CD14-positive cells in an amount of $3 \times 10^4$ cells were subjected to 6 days of suspension culture using a 6-well dish coated with Ultra-Low Attachment Surface (#3471; CORNING) in Stemline II supplemented with GM-CSF (50 ng/mL) +IL-4 (40 ng/mL) and ITS.

Example 2

Figure 2:
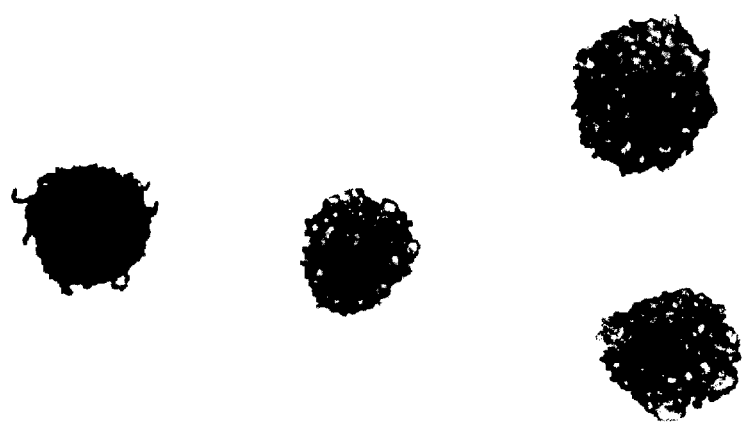
FIG. 2 shows a photograph of a May-Giemsa-stained image of dendritic cells derived from iPS cells after suspension culture.

By the following method, human iPS cells (253G4) were induced to differentiate into dendritic cells through CD14-positive monocyte, and the obtained cells were subjected to May-Giemsa staining. As a result, it was confirmed that the obtained cells had a shape similar to that of dendritic cells derived from peripheral blood (FIG. 2).
1. iPS cell colonies were plated on a 6-well dish coated with growth factor-reduced Matrigel such that not more than 5 colonies were contained in each well, and cultured using mTeSR1 until the diameter of each colony became about 1 mm.
2. The medium was replaced with Stemline II supplemented with ITS and 20 ng/mL BMP4, and the cells were cultured for 4 days.
3. The medium was replaced with Stemline II supplemented with ITS, 50 ng/mL VEGF and 50 ng/mL SCF, and the cells were cultured for 2 days.
4. The medium was replaced with Stemline II supplemented with ITS, 50 ng/mL SCF, 50 ng/mL IL-3, 5 ng/mL TPO and 50 ng/mL Flt-3 ligand, and the cells were cultured for 7 to 9 days.
5. The medium was replaced with Stemline II supplemented with ITS, 50 ng/mL Flt-3 ligand, 25 ng/mL GM-CSF and 50 ng/mL M-CSF, and the cells were cultured for 15 days.
6. Floating cells in the culture supernatant were collected, and dead cells were removed by density gradient centrifugation using Lymphoprep, followed by separation of CD14-positive cells using CD14 MicroBeads with autoMACS pro. The separated CD14-positive cells in an amount of $3 \times 10^4$ cells were subjected to 5 days of suspension culture using a 6-well dish coated with Ultra-Low Attachment Surface in Stemline II supplemented with ITS, 25 ng/mL GM-CSF and 40 ng/mL IL-4. Further, 0.2 ng/mL TNF-α and 1.0 μg/ml LPS were added to the medium, and the culture was continued for 2 days.

Example 3

Figure 3:
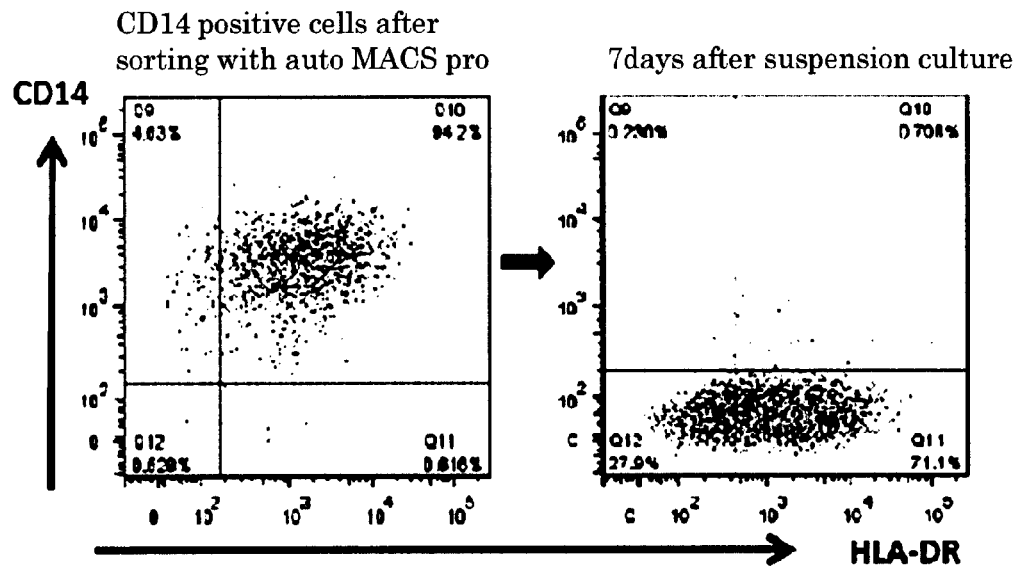
FIG. 3 shows results of flow cytometry of cells obtained before suspension culture (left) and after 7 days of suspension culture (right) of CD14-positive cells.
Figure 4:
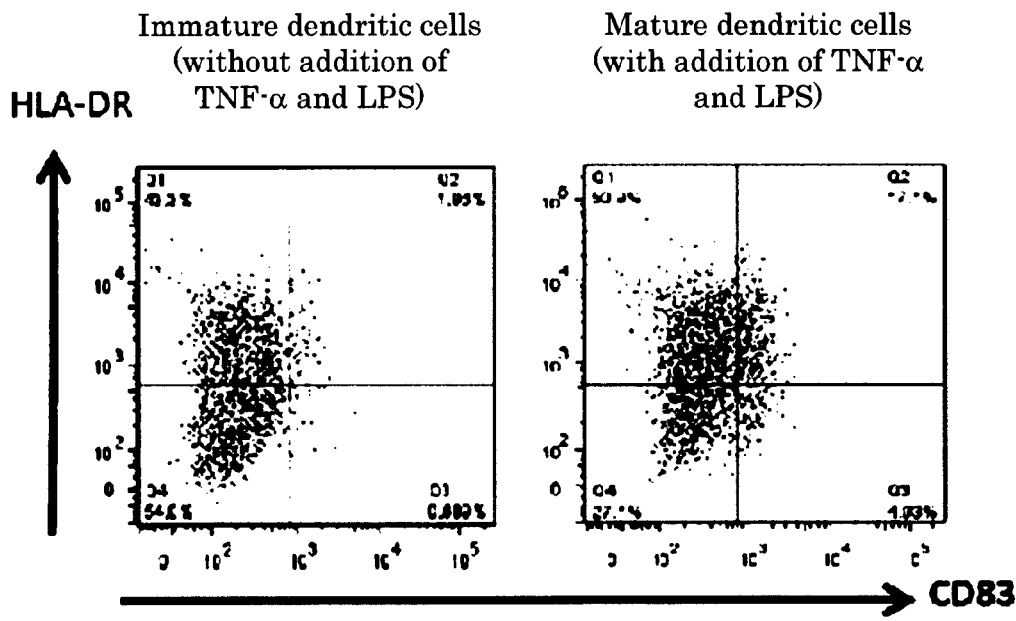
FIG. 4 shows results of flow cytometry of immature dendritic cells or mature dendritic cells respectively obtained by non-treating or treating immature dendritic cells with TNF-α and LPS.

By the following method, human iPS cells (253G4) were induced to differentiate into dendritic cells through CD14-positive monocyte, and the obtained cells were then analyzed by flow cytometry (FIGS. 3 and 4). As a result, it was confirmed that addition of TNF-α and LPS in Step 6 resulted in a larger number of cells which are positive for HLA-DR and CD83. That is, it was suggested that, by the step of culturing in a medium supplemented with TNF-α and LPS, maturation of dendritic cells is attained.

Figure 5:
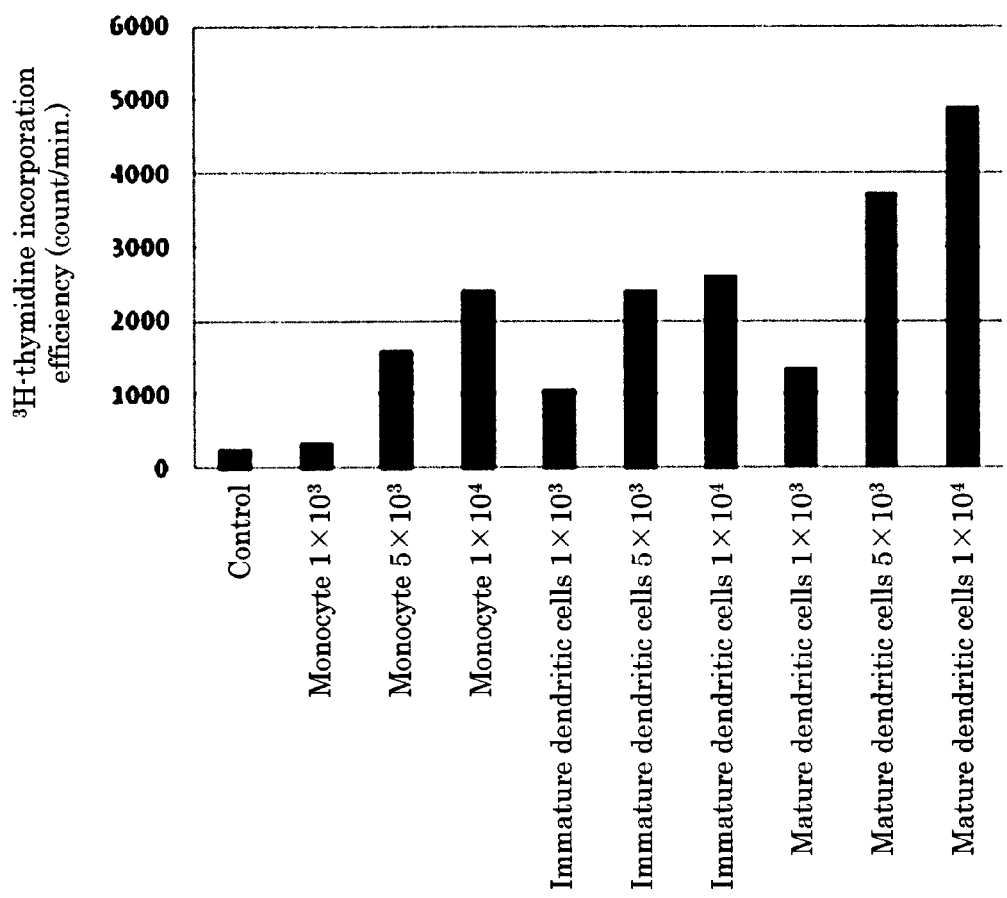
FIG. 5 shows results of cell proliferation assay for naïve T cells after contacting with monocyte or immature dendritic cells or mature dendritic cells derived from iPS cells.

Furthermore, proliferation activity of naïve T cells after contacting with monocyte, immature dendritic cells or mature dendritic cells differentiated from iPS cells was tested with $^3$H-thymidine incorporation assay (FIG. 5). As the result, it was confirmed that the mature dendritic cells differentiated from iPS cells possessed growth stimulation efficiency for naïve T cell.

1. iPS cell colonies were plated on a 6-well dish coated with growth factor-reduced Matrigel such that not more than 5 colonies were contained in each well, and cultured using mTeSR1 until the diameter of each colony became about 1 mm.
2. The medium was replaced with Stemline II supplemented with ITS and 20 ng/mL BMP4, and the cells were cultured for 4 days.
3. The medium was replaced with Stemline II supplemented with ITS, 50 ng/mL VEGF, 25 ng/ml bFGF (#133-FB-025; R&D Systems) and 50 ng/mL SCF, and the cells were cultured for 2 days.
4. The medium was replaced with Stemline II supplemented with ITS, 50 ng/mL SCF, 50 ng/mL IL-3, 5 ng/mL TPO and 50 ng/mL Flt-3 ligand, and the cells were cultured for 7 to 9 days.
5. The medium was replaced with Stemline II supplemented with ITS, 50 ng/mL Flt-3 ligand, 25 ng/mL GM-CSF and 50 ng/mL M-CSF, and the cells were cultured for 15 days.
6. Floating cells in the culture supernatant were collected, and dead cells were removed by density gradient centrifugation using Lymphoprep, followed by separation of CD14-positive cells using CD14 MicroBeads with autoMACS pro. The separated CD14-positive cells (use as monocyte) in an amount of $1.5 \times 10^6$ cells were subjected to suspension culture using a 6-well dish coated with Ultra-Low Attachment Surface in (i) Stemline II supplemented with ITS, 25 ng/mL GM-CSF and 40 ng/mL IL-4 for 7 days (use as immature dendritic cells) or in (ii) Stemline II supplemented with ITS, 25 ng/mL GM-CSF, 40 ng/mL IL-4 for 5 days, followed by addition of 0.2 ng/mL TNF-α and 1 μg/mL LPS, and the culture was continued for additional 2 days. (use as mature dendritic cells).

Example 4

Other basal media were tested whether the differentiation efficiency was changed or not. As a result, the dendritic cells were obtained from iPS cells by the following method.
1. iPS cell colonies were plated on a 6-well dish coated with growth factor-reduced Matrigel such that not more than 5 colonies were contained in each well, and cultured using mTeSR1 until the diameter of each colony became about 1 mm.
2. The medium was replaced with StemPro-34SFM (#10639-011; Invitrogen) supplemented with 80 ng/mL BMP4, and the cells were cultured for 4 days.
3. The medium was replaced with StemPro-34SFM supplemented with 100 ng/mL VEGF, 25 ng/ml bFGF and 100 ng/mL SCF, and the cells were cultured for 2 days.
4. The medium was replaced with StemPro-34SFM supplemented with 50 ng/mL SCF, 50 ng/mL IL-3, 5 ng/mL TPO and 50 ng/mL Flt-3 ligand, and the cells were cultured for 7 days to 9 days.
5. The medium was replaced with StemPro-34SFM supplemented with 50 ng/mL Flt-3 ligand, 25 ng/mL GM-CSF and 50 ng/mL M-CSF, and the cells were cultured for 3 days to 15 days. During this culture, the medium was replaced with fresh medium every 5 days.
6. Floating cells in the culture supernatant were collected, and dead cells were removed by density gradient centrifugation using Lymphoprep, followed by separation of CD14-positive cells using CD14 MicroBeads with autoMACS pro. The separated CD14-positive cells in an amount of $1.5 \times 10^6$ cells were subjected to suspension culture using a 6-well dish coated with Ultra-Low Attachment Surface in StemPro-34SFM supplemented with 25 ng/mL GM-CSF and 40 ng/mL IL-4. On Day 5 of the suspension culture, 1 μg/mL LPS and 0.2 ng/mL TNF-α were added to the medium, and the culture was continued for additional 2 days.

INDUSTRIAL APPLICABILITY

By the present invention, dendritic cells can be prepared from pluripotent stem cells such as ES cells or iPS cells. The produced dendritic cells are effective for treatment such as cancer immunotherapy, or development of therapeutic methods of autoimmune diseases or the like in which dendritic cells are involved.

What is claimed is:
1. A method for producing dendritic cells from mammalian pluripotent stem cells, said method comprising culturing pluripotent stem cells by the steps below:
   (1) culturing the pluripotent stem cells in an adherent culture comprising a medium which comprises bone morphogenic protein 4 (BMP4) but does not comprise serum;
   (2) culturing the cells obtained by step (1) in an adherent culture comprising a medium which comprises vascular endothelial growth factor (VEGF), basic fibroblast growth factor (bFGF) and/or stem cell factor (SCF) but does not comprise serum;
   (3) culturing the cells obtained by step (2) in an adherent culture comprising a medium which comprises a hematopoietic factor but does not comprise serum, wherein said culturing in step (3) is performed in a first medium comprising hematopoietic factors consisting of (i) SCF, thrombopoietin (TPO), interleukin-3 (IL-3) and Fms-like tyrosine kinase 3 ligand (Flt3-ligand), and then in a second medium comprising hematopoietic factors consisting of (ii) granulocyte macrophage-colony stimulating factor (GM-CSF), macrophage-colony stimulating factor (M-CSF) and Flt3-ligand; and
   (4) culturing the cells obtained by step (3) in a suspension culture comprising a medium which comprises GM-CSF and interleukin-4 (IL-4) but does not comprise serum, wherein dendritic cells are produced/collected.
2. The method according to claim 1, wherein said adherent culture in said Steps (1) to (3) is performed in an extracellular matrix-coated dish.
3. The method according to claim 2, wherein said extracellular matrix is a reconstituted basement membrane preparation extracted from Engelbreth-Holm-Swarm mouse sarcoma cells.
4. The method according to claim 1, wherein the suspension culture medium in Step (4), comprises a medium comprising lipopolysaccharide (LPS) and tumor necrosis factor-α (TNF-α).
5. The method according to claim 1, wherein said dendritic cell is positive for HLA-DR and negative for CD14.
6. The method according to claim 5, wherein said dendritic cell is positive for CD83.
7. The method according to claim 1, wherein Step (1) is performed for 4 days.
8. The method according to claim 1, wherein Step (2) is performed for 2 days.
9. The method according to claim 1, wherein said pluripotent stem cell is a human iPS cell.
10. A method for producing dendritic cells from mammalian pluripotent stem cells, said method comprising culturing pluripotent stem cells by the steps below:

(1) culturing the pluripotent stem cells in an adherent culture comprising a medium which comprises bone morphogenic protein 4 (BMP4) but does not comprise serum;
(2) culturing the cells obtained by step (1) in an adherent culture comprising a medium which comprises vascular endothelial growth factor (VEGF), basic fibroblast growth factor (bFGF) and/or stem cell factor (SCF) but does not comprise serum;
(3) culturing the cells obtained by step (2) in an adherent culture comprising a medium which comprises a hematopoietic factor but does not comprise serum, wherein said culturing in step (3) is performed in a first medium comprising hematopoietic factors consisting of (i) SCF, thrombopoietin (TPO), interleukin-3 (IL-3) and Fms-like tyrosine kinase 3 ligand (Flt3-ligand), and then in a second medium comprising hematopoietic factors consisting of (ii) granulocyte macrophage-colony stimulating factor (GM-CSF), macrophage-colony stimulating factor (M-CSF), Flt3-ligand, and SCF; and
(4) culturing the cells obtained by step (3) in a suspension culture comprising a medium which comprises GM-CSF and interleukin-4 (IL-4) but does not comprise serum, wherein dendritic cells are produced/collected.

11. The method according to claim 10, wherein said adherent culture in said Steps (1) to (3) is performed in an extracellular matrix-coated dish.

12. The method according to claim 11, wherein said extracellular matrix is a reconstituted basement membrane preparation extracted from Engelbreth-Holm-Swarm mouse sarcoma cells.

13. The method according to claim 10, wherein the suspension culture medium in Step (4), comprises a medium comprising lipopolysaccharide (LPS) and tumor necrosis factor-α (TNF-α).

14. The method according to claim 10, wherein said dendritic cell is positive for HLA-DR and negative for CD14.

15. The method according to claim 14, wherein said dendritic cell is positive for CD83.

16. The method according to claim 10, wherein Step (1) is performed for 4 days.

17. The method according to claim 10, wherein Step (2) is performed for 2 days.

18. The method according to claim 10, wherein said pluripotent stem cell is a human iPS cell.

* * * * *